United States Patent
Pan (10) Patent No.: US 9,017,295 B2
(45) Date of Patent: Apr. 28, 2015

(54) SYRINGE ADAPTER WITH A BALL-TYPED VALVE

(75) Inventor: Hsiu-Feng Pan, Shulin (TW)

(73) Assignee: Skill Partner Limited, Apia (WS)

( * ) Notice: Subject to any disclaimer, the term of this patent is extended or adjusted under 35 U.S.C. 154(b) by 757 days.

(21) Appl. No.: 12/874,275

(22) Filed: Sep. 2, 2010

(65) Prior Publication Data

US 2012/0059334 A1 Mar. 8, 2012

(51) Int. Cl.
*A61M 5/00* (2006.01)
*A61M 39/10* (2006.01)
*A61M 39/24* (2006.01)

(52) U.S. Cl.
CPC ....... *A61M 39/10* (2013.01); *A61M 2039/1077* (2013.01); *A61M 2039/2473* (2013.01); *Y10S 604/905* (2013.01)

(58) Field of Classification Search
USPC .................. 604/246, 249, 122–127, 537, 905
See application file for complete search history.

(56) References Cited

U.S. PATENT DOCUMENTS

| 5,782,816 A | 7/1998 | Werschmidt et al. |
| 6,228,069 B1 * | 5/2001 | Barth et al. ................... 604/249 |
| 7,520,489 B2 | 4/2009 | Ruschke et al. |
| 2005/0010177 A1 | 1/2005 | Tsai |
| 2006/0293629 A1 * | 12/2006 | Cote et al. ..................... 604/246 |

FOREIGN PATENT DOCUMENTS

| EP | 0696461 A2 | 2/1996 |
| EP | 2161053 A1 | 3/2010 |
| WO | 2010111546 A2 | 9/2010 |

OTHER PUBLICATIONS

Search report dated Feb. 24, 2011 for corresponding United Kingdom application No. GB1021514.3

* cited by examiner

*Primary Examiner* — Aarti B Berdichevsky
*Assistant Examiner* — Laura Schell
(74) *Attorney, Agent, or Firm* — Bacon & Thomas, PLLC (57) ABSTRACT

A syringe adapter with a ball-typed valve has a base, a dosing tube mounted around the base and a resilient valve mounted in the base and the dosing tube. The base has a guiding groove and an inner liquid channel communicating with each other, as well as an exhaust channel. Liquid medicine injected into the syringe adapter flows through the guiding groove and causes the inner liquid channel to be injected into a patient's body. The liquid medicine remaining in the split is cleaned when cleaning fluid is injected to clean the syringe adapter. Air in the syringe adapter flows out through the exhaust channel and is not injected into the patient's body, so the patient is free from pain. Furthermore, elements and assembling processes of the syringe adapter are simplified and manufacturing cost of the syringe adapter is lowered.

20 Claims, 10 Drawing Sheets

SYRINGE ADAPTER WITH A BALL-TYPED VALVE

BACKGROUND OF THE INVENTION

1. Field of the Invention

The present invention relates to a syringe adapter with a ball-typed valve, especially to a syringe adapter that allows a needleless syringe to inject liquid medicine therethrough.

2. Description of the Prior Art(s)

In order to reduce needle shots for patients undergoing medical examinations like a blood test, a syringe adapter is mounted on a delivery pipe of an intravenous bag or mounted directly on the patient. By so doing, nutrition or liquid medicine can be injected into the patient through the syringe adapter and the patient does not have to go through the discomfort of repeated injections.

A conventional syringe adapter, such as a BI-DIRECTIONAL VALVE AND METHOD OF USING SAME (U.S. Pat. No. 5,782,816) or a FLUID HANDLING DEVICE AND METHOD OF MAKING SAME (U.S. Pat. No. 7,520,489), has a dosing tube and a resilient valve. The resilient valve is mounted in the dosing tube. The resilient valve has a peripheral protrusion formed around the resilient valve and abutting an inner surface of the dosing tube to securely seal the open ends of the dosing tube when the conventional syringe adapter is not in use. Thus, when a needleless syringe is inserted into the dosing tube, the resilient valve is pressed and arced, so a flowing space is formed between the resilient valve, the open ends and the inner surface of the dosing tube. Then, liquid medicine is injected into a patient through the conventional syringe adapter.

However, the conventional syringe adapter has the following disadvantages. When the needleless syringe is drawn out from the syringe adapter, a negative pressure causes the blood of the patient or the liquid medicine to flow back to and remain in the conventional syringe adapter. Consequently, when injecting again, the blood and the liquid medicine remaining in the conventional syringe adapter is injected back into the patient's body, putting the patient at the risk of infection. Furthermore, air remaining in the dosing tube is also injected into the patient's body. The patient's blood vessel is expanded by the air, causing patient discomfort.

Another conventional syringe adapter, such as a NEEDLELESS ACCESS DEVICE (U.S. Pat. No. 6,228,069), has a tubular body, a cap mounted on and around the body, and a plunger and a spring mounted in the body. The plunger is pulled by the spring and selectively seals an open end of the body. A channel that allows the liquid medicine to flow through and a vent that allows the air in the body to flow out of the conventional syringe adapter are defined between the body and the cap so the air is not injected into the patient's body.

Since the plunger is pulled by the spring, at least four elements for assembling the abovementioned conventional syringe adapter are needed. Thus, manufacturing cost of the conventional syringe adapter is high and manufacturing processes of the conventional syringe adapter is complicated. Moreover, since the metal spring affects the result of a magnetic resonance imaging (MRI) scan, the patient cannot wear the conventional syringe adapter during a MRI check-up. In that case, the intended effect of the conventional syringe adapter, that is, reducing the needle shots for the patients, is not achieved.

To overcome the shortcomings, the present invention provides a syringe adapter with a ball-typed valve to mitigate or obviate the aforementioned problems.

SUMMARY OF THE INVENTION

The main objective of the present invention is to provide a syringe adapter with a ball-typed valve. The syringe adapter has a base, a dosing tube mounted around the base and a resilient valve mounted in the base and the dosing tube. The base has a guiding groove and an inner liquid channel communicating with each other, as well as an exhaust channel.

Liquid medicine injected into the syringe adapter flows through the guiding groove and causes the inner liquid channel to be injected into a patient's body. The liquid medicine remaining in the split is cleaned when cleaning fluid is injected to clean the syringe adapter. Air in the syringe adapter flows out through the exhaust channel and is not injected into the patient's body, so the patient is free from pain. Furthermore, elements and assembling processes of the syringe adapter are simplified and manufacturing cost of the syringe adapter is lowered.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
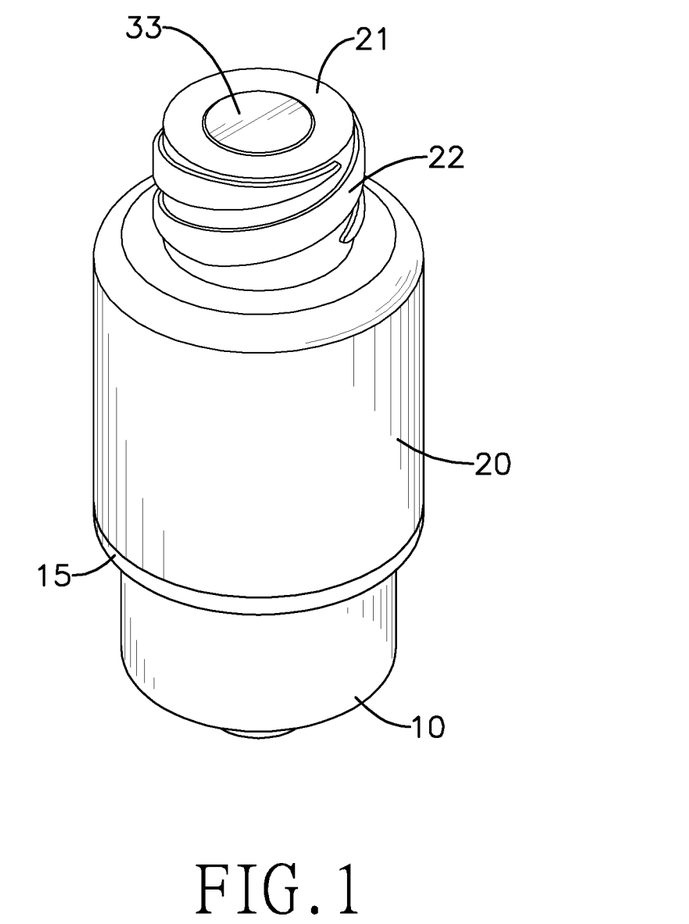
FIG. 1 is a perspective view of a first embodiment of a syringe adapter with a ball-typed valve in accordance with the present invention.
Figure 4:
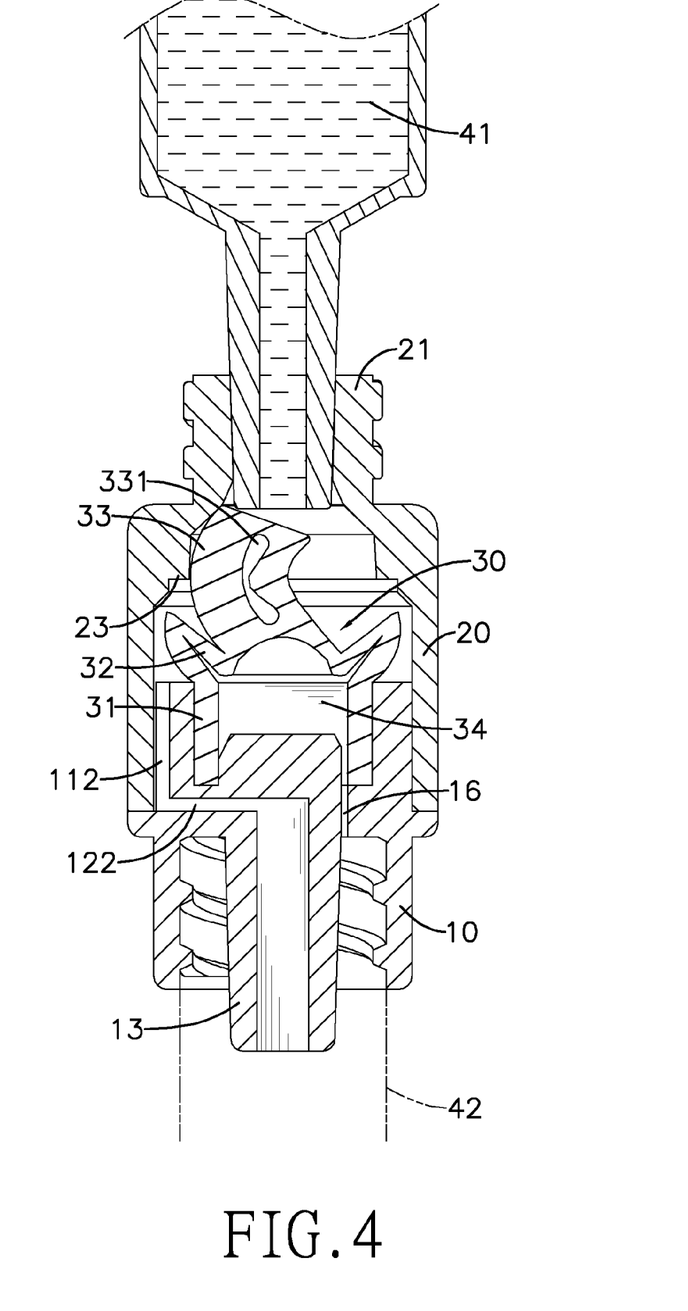
FIG. 4 is an operational cross-sectional side view of the syringe adapter in FIG. 1.

With reference to FIGS. 1 and 4, a syringe adapter with a ball-typed valve in accordance with the present invention is connected to a delivery pipe 42 that is connected to a patient through a needle. Thus, a needleless syringe 41 injects liquid medicine into the patient through the syringe adapter and the delivery pipe 42.

Figure 2:
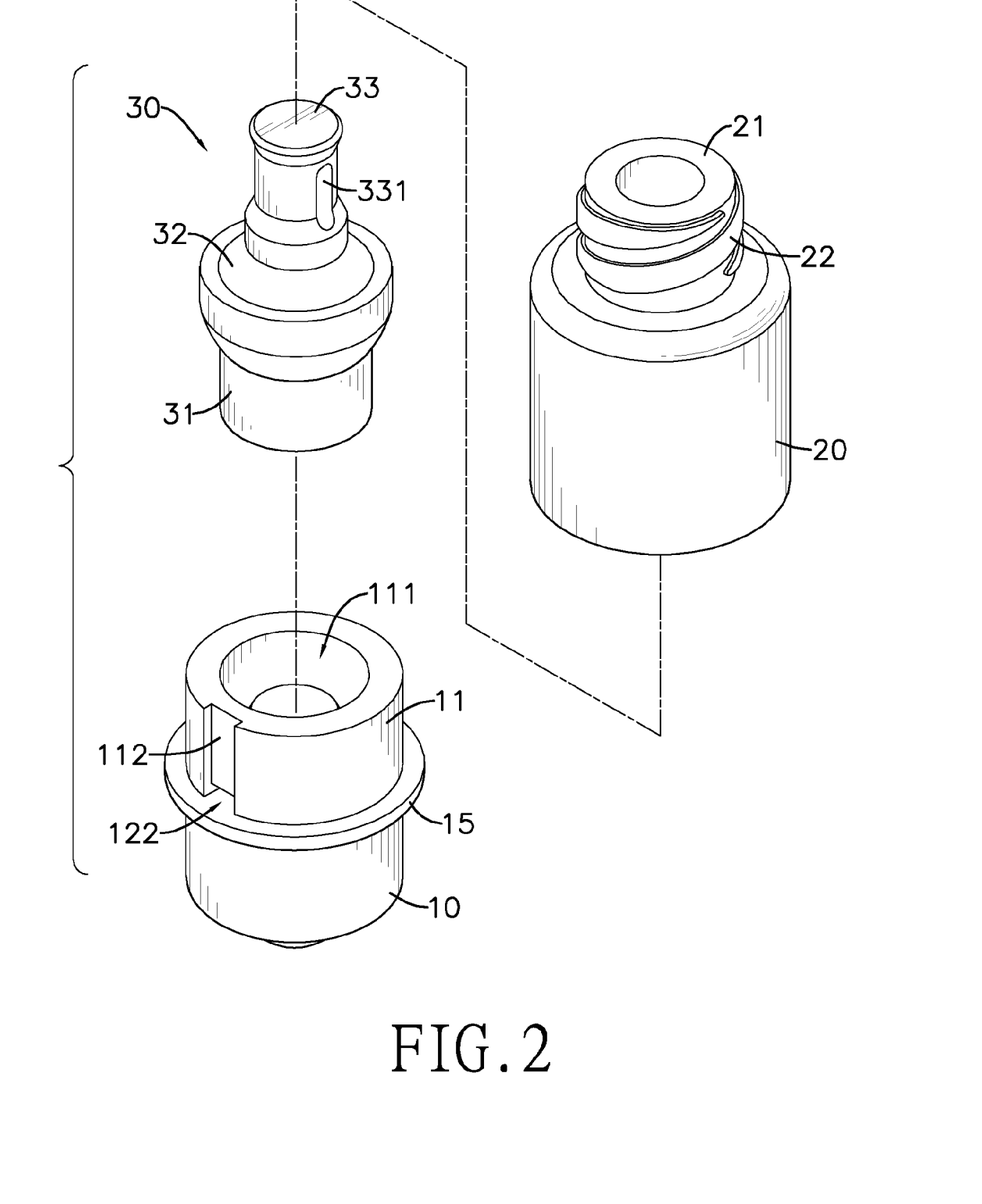
FIG. 2 is an exploded perspective view of the syringe adapter in FIG. 1.

With further reference to FIG. 2, the syringe adapter in accordance with the present invention comprises a base 10, a dosing tube 20 and a resilient valve 30.

Figure 3:
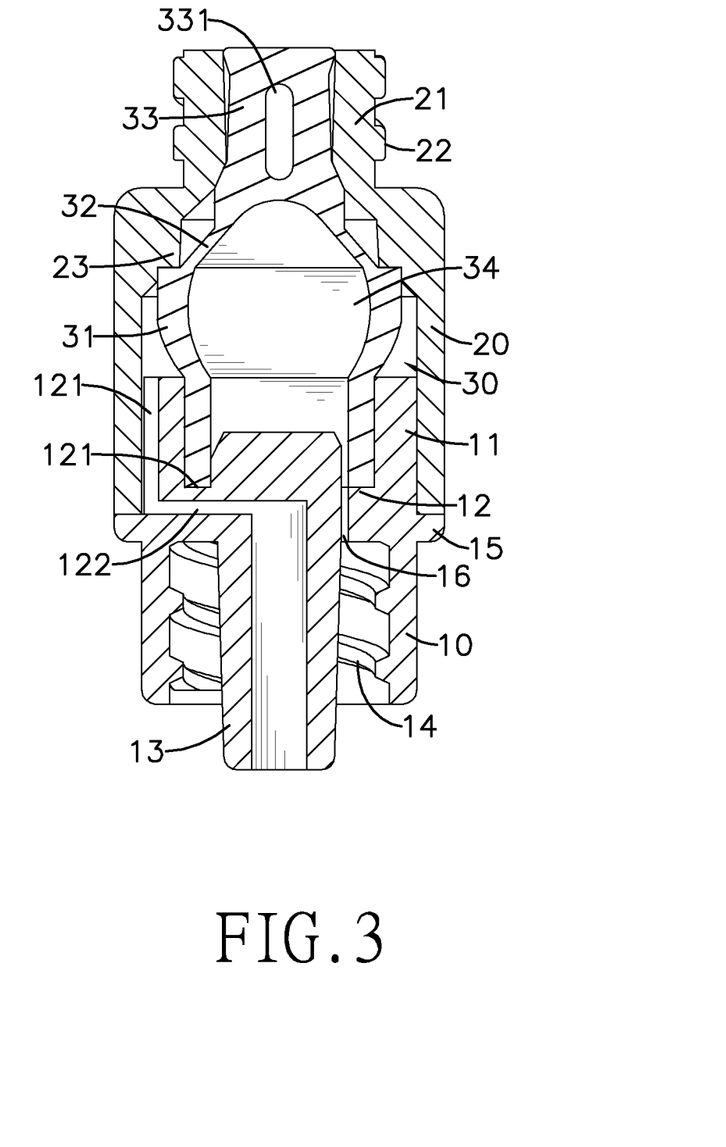
FIG. 3 is a cross-sectional side view of the syringe adapter in FIG. 1.
Figure 5:
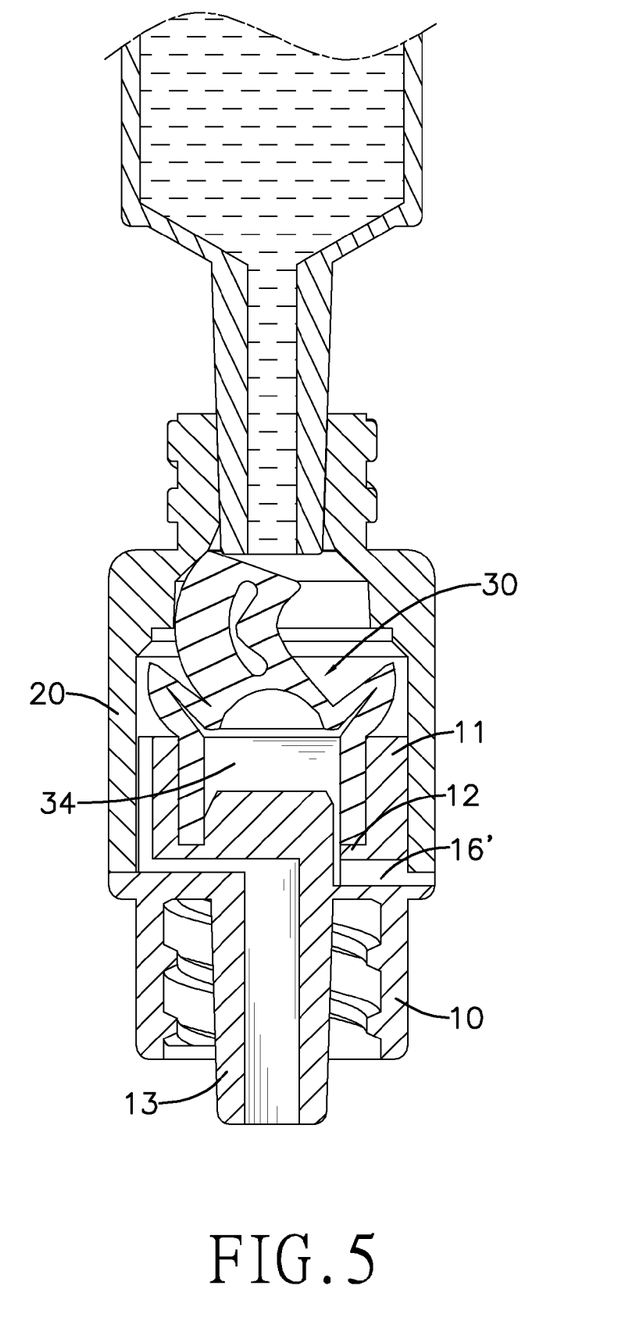
FIG. 5 is an operational cross-sectional side view of a second embodiment of a syringe adapter with a ball-typed valve in accordance with the present invention.

With further reference to FIGS. 3 and 5, the base 10 is tubular in shape and has a circular wall 11, a bottom 12, a connecting tube 13, an inner thread 14, a flange 15 and an exhaust channel 16, 16'.

The circular wall 11 is formed on and around the base 10 and has an outer surface, an inner surface, a mounting recess 111 and a guiding groove112. The mounting recess 111 is defined in the circular wall 11. The guiding groove 112 is formed in the outer surface of the circular wall 11.

The bottom 12 is formed in the mounting recess 111 and has an upper surface, a circular groove 121 and an inner liquid channel 122. The upper surface of the bottom 12 corresponds to the mounting recess 111. The circular groove 121 is formed in the upper surface of the bottom 12. The inner liquid channel 122 is formed transversely through the bottom 12 and communicates with the guiding groove 112 of the circular wall 11.

The connecting tube 13 protrudes down from the base 10. The connecting tube 13 communicates with the inner liquid channel 122 of the bottom 12 and is connected with the delivery pipe 42. The inner thread 14 is formed around an inner surface of the connecting tube 13 of the base 10, so the base 10 can be screwed to other pipes through the inner thread 14. The flange 15 is formed around an outer surface of the base 10.

The exhaust channel 16, 16' is formed through the base 10. The exhaust channel 16, 16' communicates the mounting recess 111 with an outside of the syringe adapter and does not communicate with the inner liquid channel 122 of the bottom 12. With reference to FIG. 4, the exhaust channel 16 may be formed longitudinally through the bottom 12 and communicates with the connecting tube 13. With reference to FIG. 5, in a second preferred embodiment of the syringe adapter, the exhaust channel 16' may be formed transversely through the bottom 12, the circular wall 11 and the flange 15.

The dosing tube 20 is tubular in shape and mounted securely around the outer surface of the circular wall 11 of the base 10. The dosing tube 20 abuts the flange 15 of the base 10 and has an injection tube 21 and a stop 23. The injection tube 21 protrudes up from a top of the dosing tube 20. The injection tube 21 communicates with the mounting recess 111 of the base 10 and has an outer thread 22 formed around an outer surface of the injection tube 21. Thus, the dosing tube 20 can be screwed to the needle-less syringe 41 through the outer thread 22. The stop 23 is formed on an inner surface of the dosing tube 20 adjacent to the top of the dosing tube 20.

The resilient valve 30 is silicon and hollow, and is formed integrally as a single part of the same material. The resilient valve 30 is mounted in the mounting recess 111 of the base 10 and the dosing tube 20, and has a positioning ring 31, a bendable portion 32, a plunger 33 and an air chamber 34.

The positioning ring 31 is mounted on the bottom 12 of the base 10, corresponds to the inner surface of the circular wall 11 of the base 10 and has a lower end, an upper end and a thickness. The lower end of the positioning ring 31 is mounted in the circular groove 121 of the bottom 12 of the base 10. The upper end of the positioning ring 31 selectively abuts the stop 23 of the dosing tube 20.

The bendable portion 32 is formed around the upper end of the positioning ring 31 and has a thickness thinner than the thickness of the positioning ring 31, so the bendable portion 32 is more easily bent than the positioning ring 31.

The plunger 33 is formed on the bendable portion 32 and protrudes into the injection tube 21 of the dosing tube 20 to seal the injection tube 21 and has a through hole 331 formed transversely through the plunger 33, so the plunger 33 is also bendable.

The air chamber 34 is defined in the positioning ring 31, the bendable portion 32 and the plunger 33 and communicates with the exhaust channel 16, 16' of the base 10.

With further reference to FIG. 3, before the needle-less syringe 41 is inserted into the injection tube 21 of the dosing tube 20, the plunger 33 of the resilient valve 30 protrudes in and seals the injection tube 21.

With further reference to FIG. 4, when the needleless syringe 41 is inserted into the injection tube 21 of the dosing tube 20, the plunger 33 of the resilient valve 30 is pushed so the bendable portion 32 and the plunger 33 of the resilient valve 30 are bent and the upper end of the positioning ring 31 of the resilient valve 30 is detached from the stop 23 of the dosing tube 20.

Thus, the liquid medicine in the needle-less syringe 41 is injected into the dosing tube 20, filling the space between the resilient valve 30 and the dosing tube 20. The liquid medicine then flows through the guiding groove 112, the inner liquid channel 122 and the connecting tube 13 of the base 10 and is injected into the patient's body through the delivery pipe 42 and the needle.

Furthermore, when the bendable portion 32 of the resilient valve 30 is pushed and bent by the needleless syringe 41, air in the air chamber 34 of the resilient valve 30 is discharged to the outside of the syringe adapter through the exhaust channel 16, 16' of the base 10 to facilitate the pushing of the resilient valve 30. Since the liquid medicine and the air flow through different paths, the air is not injected into the patient's body and the patient is free from pain.

Figure 6:
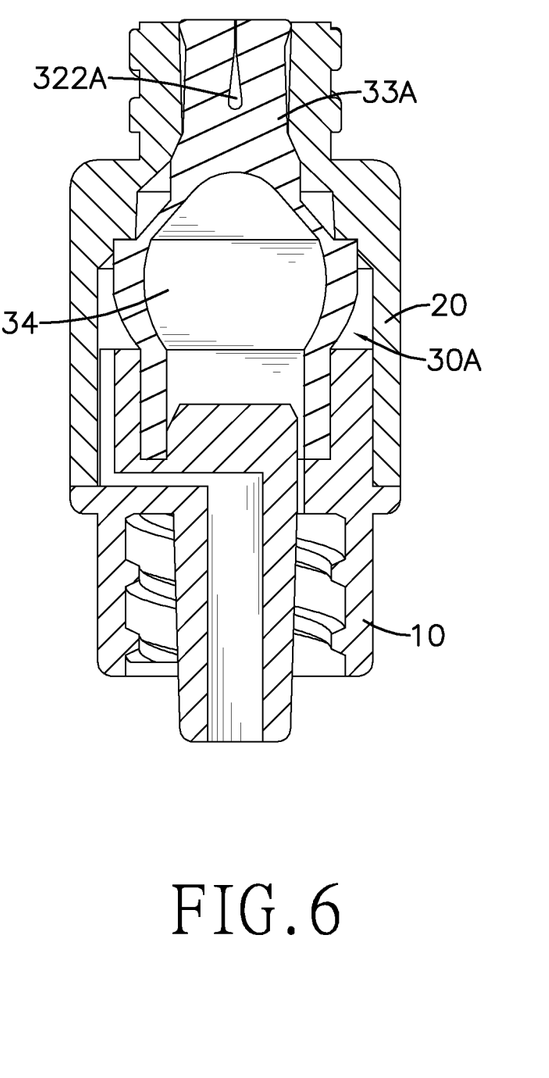
FIG. 6 is a cross-sectional side view of a third embodiment of a syringe adapter with a ball-typed valve in accordance with the present invention.

With further reference to FIG. 6, in a third preferred embodiment of the syringe adapter, the plunger 33A of the resilient valve 30A has a split 332A formed in a top of the plunger 33A. When the plunger 33A protrudes into the injection tube 21 of the dosing tube 20, the plunger 33A is pressed and the split 332A is sealed.

Figure 7:
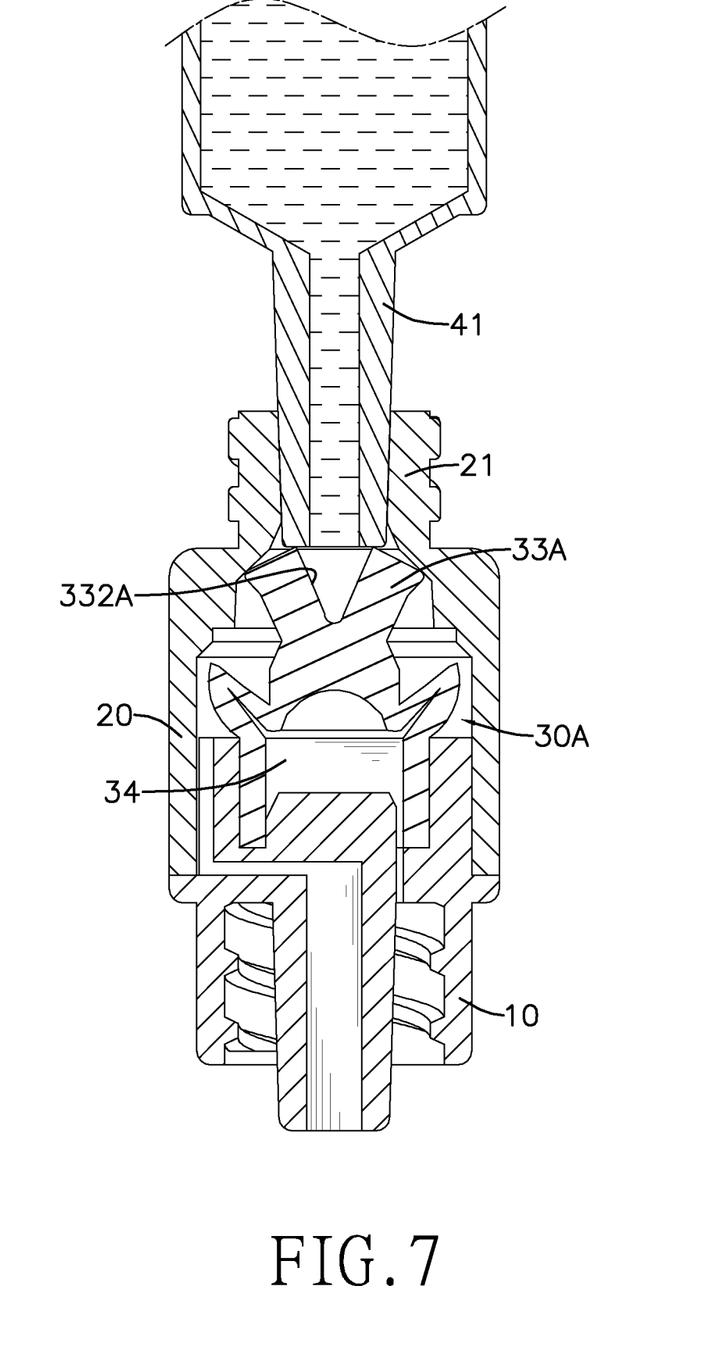
FIG. 7 is an operational cross-sectional side view of the syringe adapter in FIG. 6.

With further reference to FIG. 7, when the needleless syringe 41 pushes the plunger 33A of the resilient valve 30A, the plunger 33A opens up and the split 332A becomes a space that is triangular in shape in cross-section and allows the liquid medicine to flow through. The plunger 33A with the split 332A that opens up whenever the needle-less syringe 41 pushes the plunger 33A ensures that the liquid medicine can be injected into the syringe adapter. Consequently, the liquid medicine remaining in the split 332A is also cleaned when cleaning fluid is injected to clean the syringe adapter.

Figure 8:
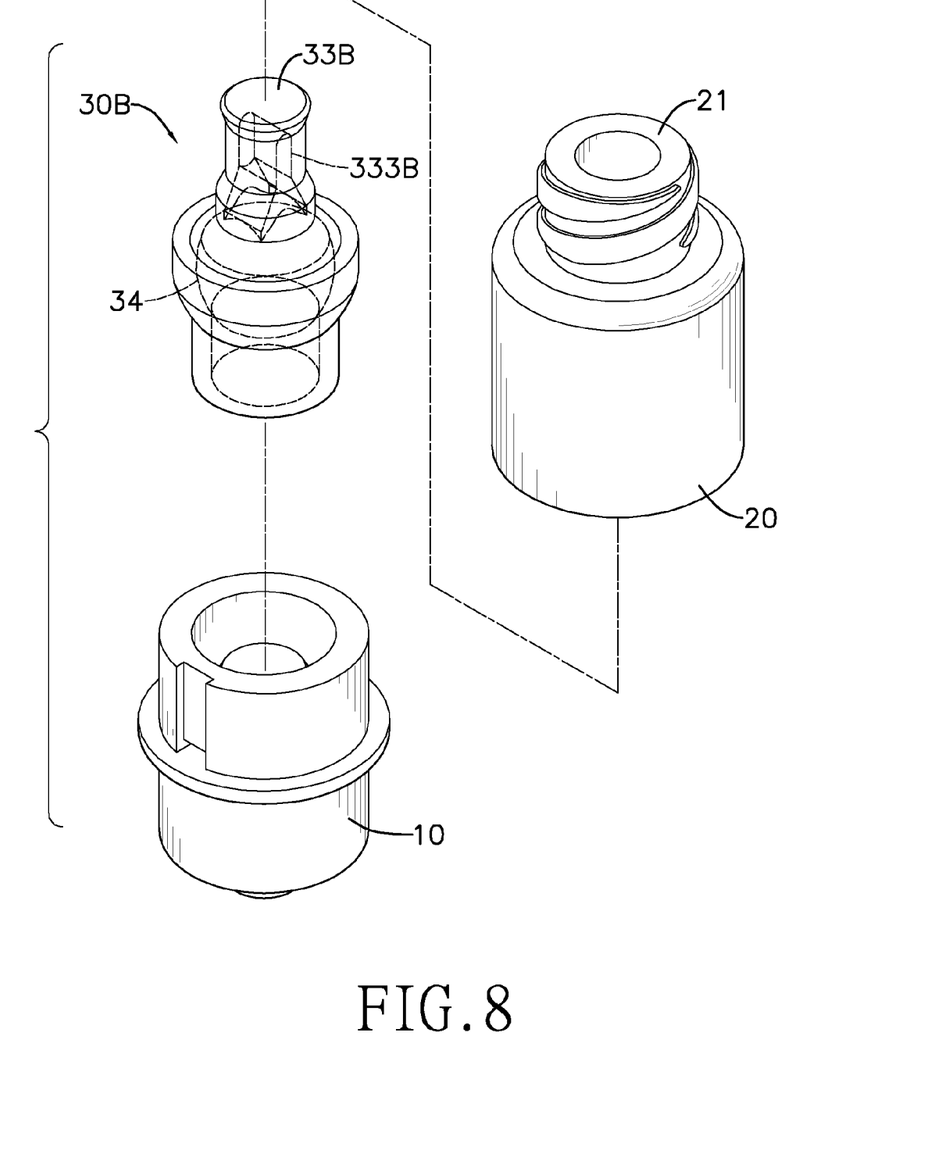
FIG. 8 is an exploded perspective view of a fourth embodiment of a syringe adapter with a ball-typed valve in accordance with the present invention.
Figure 9:
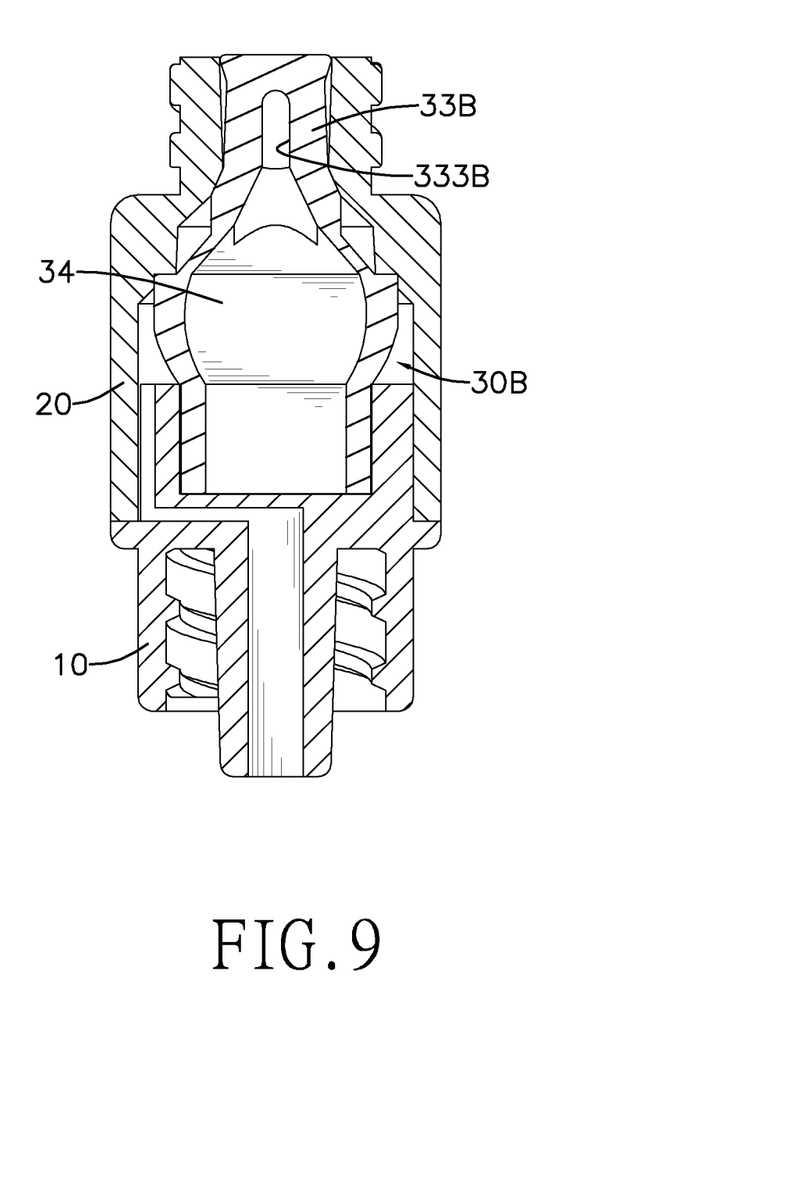
FIG. 9 is a cross-sectional side view of the syringe adapter in FIG. 8.

With further reference to FIGS. 8 and 9, in a fourth preferred embodiment of the syringe adapter, the plunger 33B of the resilient valve 30B is hollow and has an additional chamber 33B defined in the plunger 33B, communicating with the air chamber 34 of the resilient valve 3013 and preferably, being oblate.

Figure 10:
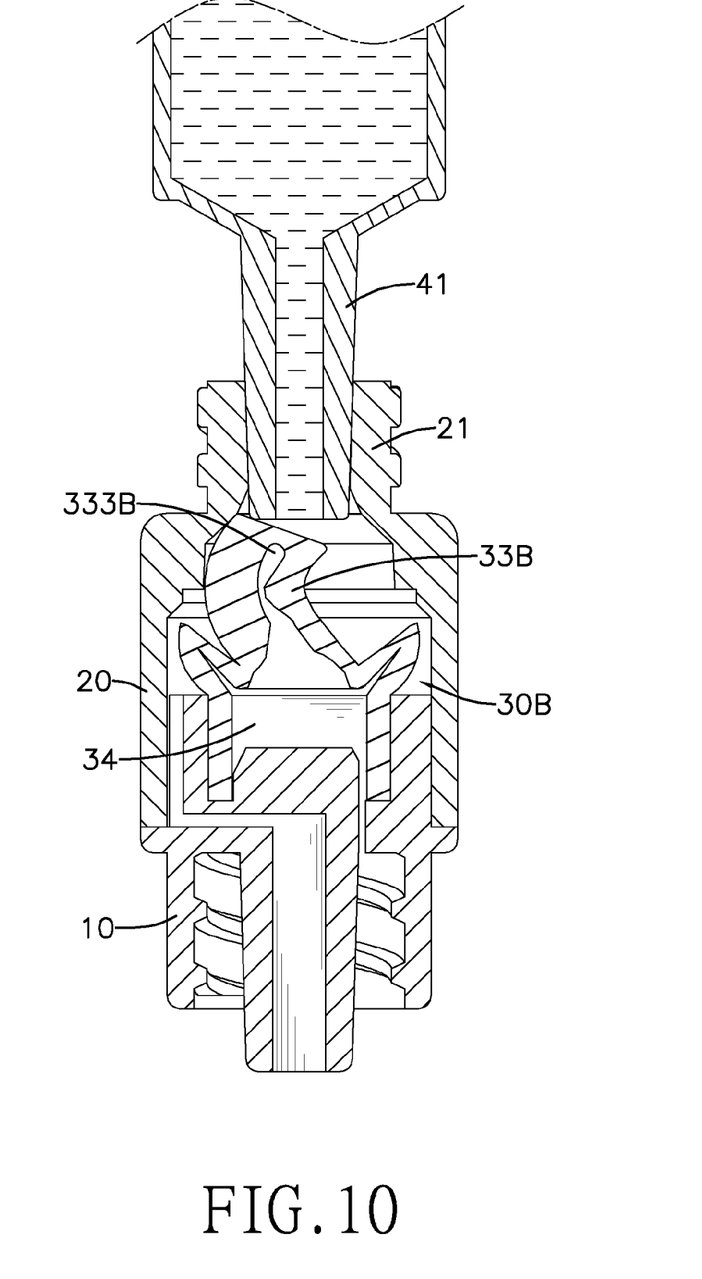
FIG. 10 is an operational cross-sectional side view of the syringe adapter in FIG. 8.

With further reference to FIG. 10, when the needleless syringe 41 pushes the plunger 33B of the resilient valve 30B, the additional chamber 333B allows the plunger 33B to be bent and the oblate additional chamber 333B further allows the plunger 33B to be bent in a specific direction. Moreover, since the additional chamber 333B is not formed through the plunger 33B, the liquid medicine does not flow through the additional chamber 333B and no liquid medicine remains in the additional chamber 333B.

The syringe adapter as described has the following advantages. Since no metal spring is needed in the syringe adapter, elements and assembling processes of the syringe adapter are simplified and manufacturing cost of the syringe adapter is lowered. In addition, the patient does not need to take off the syringe adapter while undergoing a magnetic resonance imaging (MRI) scan.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A syringe adapter comprising:
a base being tubular in shape and having
a circular wall formed on and around the base and having an outer surface;
an inner surface;
a mounting recess defined in the circular wall; and
a guiding groove formed in the outer surface of the circular wall;
a bottom formed in the mounting recess and having an inner liquid channel formed transversely through the bottom and communicating with the guiding groove of the circular wall; and
an exhaust channel formed through the base, communicating the mounting recess with an outside of the syringe adapter and not communicating with the inner liquid channel of the bottom;
a dosing tube being tubular in shape, mounted securely around the outer surface of the circular wall of the base and having
an injection tube protruding up from a top of the dosing tube and communicating with the mounting recess of the base; and
a stop formed on an inner surface of the dosing tube adjacent to the top of the dosing tube; and
a resilient valve formed integrally as a single part of the same material and mounted in the mounting recess of the base and the dosing tube, and the resilient valve having
a positioning ring mounted on the bottom of the base, corresponding to the inner surface of the circular wall of the base and having an upper end selectively abutting the stop of the dosing tube;
a bendable portion formed around the upper end of the positioning ring;
a plunger formed on the bendable portion and protruding into the injection tube of the dosing tube; and
an air chamber defined in the positioning ring, the bendable portion and the plunger and communicating with the exhaust channel of the base;
wherein when the plunger of the resilient valve is pushed toward the base, the bendable portion and the plunger of the resilient valve are bent in the dosing tube and the positioning ring of the resilient valve is detached from the stop of the dosing tube.

2. The syringe adapter as claimed in claim 1, wherein the exhaust channel of the base is formed longitudinally through the bottom.

3. The syringe adapter as claimed in claim 2, wherein the plunger of the resilient valve has a through hole formed transversely through the plunger.

4. The syringe adapter as claimed in claim 2, wherein the plunger of the resilient valve has a split formed in a top of the plunger.

5. The syringe adapter as claimed in claim 2, wherein the plunger of the resilient valve is hollow and has an additional chamber defined in the plunger and communicating with the air chamber of the resilient valve.

6. The syringe adapter as claimed in claim 2, wherein
the bottom of the base further has
an upper surface corresponding to the mounting recess of the base; and
a circular groove formed in the upper surface of the bottom;
the positioning ring of the resilient valve further has a lower end mounted in the circular groove of the bottom of the base.

7. The syringe adapter as claimed in claim 1, wherein
the base further has a flange formed around an outer surface of the base;
the exhaust channel of the base is formed transversely through the bottom, the circular wall and the flange of the base; and
the dosing tube abuts the flange of the base.

8. The syringe adapter as claimed in claim 7, wherein the plunger of the resilient valve has a through hole formed transversely through the plunger.

9. The syringe adapter as claimed in claim 7, wherein the plunger of the resilient valve has a split formed in a top of the plunger.

10. The syringe adapter as claimed in claim 7, wherein the plunger of the resilient valve is hollow and has an additional chamber defined in the plunger and communicating with the air chamber of the resilient valve.

11. The syringe adapter as claimed in claim 7, wherein
the bottom of the base further has
an upper surface corresponding to the mounting recess of the base; and
a circular groove formed in the upper surface of the bottom;
the positioning ring of the resilient valve further has a lower end mounted in the circular groove of the bottom of the base.

12. The syringe adapter as claimed in claim 11, wherein the base further has a connecting tube protruding down from the base and communicating with the inner liquid channel of the bottom.

13. The syringe adapter as claimed in claim 1, wherein the plunger of the resilient valve has a through hole formed transversely through the plunger.

14. The syringe adapter as claimed in claim 1, wherein the plunger of the resilient valve has a split formed in a top of the plunger.

15. The syringe adapter as claimed in claim 1, wherein the plunger of the resilient valve is hollow and has an additional chamber defined in the plunger and communicating with the air chamber of the resilient valve.

16. The syringe adapter as claimed in claim 1, wherein
the bottom of the base further has
an upper surface corresponding to the mounting recess of the base; and
a circular groove formed in the upper surface of the bottom;
the positioning ring of the resilient valve further has a lower end mounted in the circular groove of the bottom of the base.

17. The syringe adapter as claimed in claim 16, wherein the base further has a connecting tube protruding down from the base and communicating with the inner liquid channel of the bottom.

18. The syringe adapter as claimed in claim 6, wherein the base further has a connecting tube protruding down from the base and communicating with the inner liquid channel of the bottom.

19. The syringe adapter as claimed in claim 18, wherein
the base further has an inner thread formed around an inner surface of the connecting tube of the base; and
the injection tube of the dosing tube further has an outer thread formed around an outer surface of the injection tube.

20. The syringe adapter as claimed in claim 17, wherein
the base further has an inner thread formed around an inner surface of the connecting tube of the base; and the injection tube of the dosing tube further has an outer thread formed around an outer surface of the injection tube.

\* \* \* \* \*